United States Patent [19]

Umezawa et al.

[11] 4,374,980
[45] Feb. 22, 1983

[54] 3'-DEAMINO-3'-MORPHOLINO CARMINOMYCIN

[75] Inventors: Hamao Umezawa; Tomio Takeuchi; Kuniaki Tatsuta, all of Tokyo; Yoshikazu Takahashi, Tama, all of Japan

[73] Assignee: Zaidan Hojin Biseibutsu Kagaku Kenkyu Kai, Tokyo, Japan

[21] Appl. No.: 357,970

[22] Filed: Mar. 15, 1982

[30] Foreign Application Priority Data

Mar. 27, 1981 [JP] Japan .................. 56-44159

[51] Int. Cl.³ .................. A61K 31/71; C07H 15/24
[52] U.S. Cl. .................. 536/6.4; 424/180
[58] Field of Search .................. 536/17 A; 424/180

[56] References Cited

U.S. PATENT DOCUMENTS

| | | | |
|---|---|---|---|
| 3,590,028 | 6/1971 | Arcamone et al. | 536/17 A |
| 3,616,242 | 10/1971 | Belloc et al. | 536/17 A |
| 3,988,315 | 10/1976 | Umezawa et al. | 536/17 A |
| 4,177,264 | 12/1979 | Wu et al. | 536/17 A |
| 4,202,967 | 5/1980 | Tong et al. | 536/17 A |
| 4,301,277 | 11/1981 | Acton et al. | 536/17 A |
| 4,302,449 | 11/1981 | El Khadem et al. | 536/17 A |
| 4,303,785 | 12/1981 | Umezawa et al. | 536/17 A |
| 4,314,054 | 2/1982 | Acton et al. | 536/17 A |

FOREIGN PATENT DOCUMENTS 1426637 3/1976 United Kingdom ............. 536/17 A

OTHER PUBLICATIONS

Gause et al., "Cancer Chemotherapy Report Part 1", vol. 58, No. 2, Mar./Apr., 1974, pp. 255-256.

Primary Examiner—Johnnie R. Brown
Attorney, Agent, or Firm—David M. Morse

[57] ABSTRACT

Disclosed is 3'-deamino-3'-morpholino-carminomycin, a new anthracycline glycoside having both antimicrobial and antitumor activity. Also disclosed is a new N-alkylation procedure for preparing the above compound as well as the known anthracyclines, 3'-deamino-3'-morpholino-adriamycin and 3'-deamino-3'-morpholino-daunomycin, in high yield.

2 Claims, No Drawings

3'-DEAMINO-3'-MORPHOLINO CARMINOMYCIN

BACKGROUND OF THE INVENTION

1. Field of the Invention

This invention relates to a new anthracycline derivative, 3'-deamino-3'-morpholino-carminomycin, and pharmaceutically acceptable acid addition salts thereof. Also provided by the present invention are new and efficient processes for the preparation of two known anthracycline derivatives, 3'-deamino-3'-morpholino-daunomycin and 3'-deamino-3'-morpholino-adriamycin (including acid addition salts thereof), as well as the above-described carminomycin derivative.

2. The Prior Art

Daunomycin (U.S. Pat. No. 3,616,242) and adriamycin (U.S. Pat. No. 3,590,028) which are obtained from cultured broths of certain strains of Streptomyces have a broad antitumor spectrum against various experimental tumors and are used clinically as potent chemotherapeutic agents. The anthracycline glycoside, carminomycin (U.K. Pat. No. 1,426,637; Cancer Chemotherapy Rep. 58 (2): 255–256, 1974), has also shown activity against a variety of experimental tumors and is being evaluated clinically in the Soviet Union and other countries. While daunomycin and adriamycin and carminomycin are relatively effective as antitumor agents, their effects are by no means ideal, both with respect to spectrum of activity and toxicity problems.

Because of the recognized problems with presently available anthracyclines, extensive research has been carried out to produce new anthracycline derivatives having better antitumor activity and/or reduced toxicity. Illustrative of the newer anthracycline antitumor agents which have been reported are the following:

1. U.S. Pat. No. 3,988,315 discloses aclacinomycin A and B prepared by fermentation of *Streptomyces galilaeus*.

2. U.S. Pat 4,303,785 discloses inter alia 4'-O-tetrahydropyranyl daunomycin and adriamycin.

3. U.S. Pat No. 4,177,264 discloses N-benzyl and N,N-dibenzyl derivatives of adriamycin and daunomycin.

4. U.S. Pat No. 4,202,967 discloses N,N-pentamethylene derivatives of daunomycin and adriamycin.

5. U.S. Pat. No. 4,301,277 discloses 3'-deamino-3'-morpholino-adriamycin and 3'-deamino-3'-morpholino-daunomycin by reductive alkylation of adriamycin or daunomycin.

SUMMARY OF THE INVENTION

The present invention provides a new anthracycline glycoside antitumor antibiotic having the formula

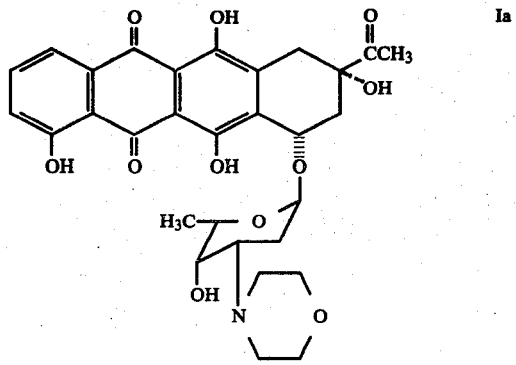

and pharmaceutically acceptable acid addition salts thereof. Also provided is a new and efficient process for producing anthracycline glycoside derivatives of the formula

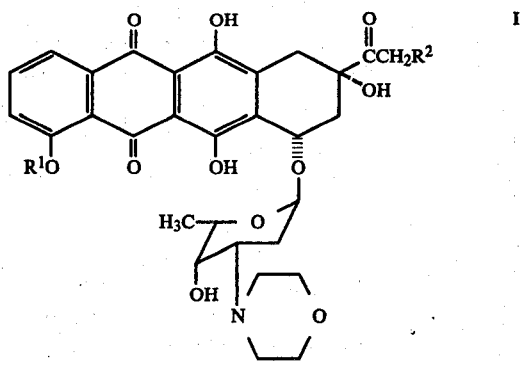

wherein $R^1$ represents hydrogen or methyl and $R^2$ represents hydrogen or hydroxyl, providing that when $R^1$ is hydrogen, $R^2$ is hydrogen, or an acid addition salt thereof, which process comprises reacting an anthracycline glycoside compound of the formula

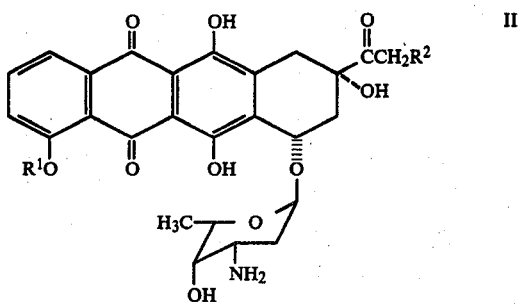

or an acid addition salt thereof with a compound of the formula

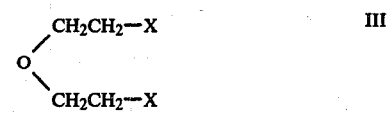

wherein X represents Br or I to convert the 3'-amino group of the anthracycline glycoside starting material to a morpholino group and, if desired, carrying out one or more of the further steps selected from (a) converting by methods known per se a product in the form of the free base or acid addition salt thereof to a pharmaceutically acceptable acid addition salt thereof or (b) converting by methods known per se a product in the form of an acid addition salt to the corresponding free base product.

As used herein and in the claims the term "pharmaceutically acceptable acid addition salt" is meant to include all those organic and inorganic acid salts of the compounds of formulae I and Ia, which salts are commonly used as substantially nontoxic salts of medicinal agents (particularly anthracycline glycosides) containing amine functions. Illustrative examples would be those salts formed from such acids as sulfuric, phosphoric, hydrochloric, hydrobromic, nitric, phosphorous, acetic, propionic, maleic, oleic, palmitic, citric, succinic, tartaric, fumaric, glutamic, pantothenic, laurylsulfonic, methanesulfonic, naphthalenesulfonic, etc.

DETAILED DESCRIPTION

U.S. Pat. No. 4,301,277 discloses preparation of 3'-deamino-3'-morpholino-adriamycin and -daunomycin by applying Borch's reductive alkylation procedure to adriamycin and daunomycin. This procedure produced the desired 3'-morpholino derivatives, but they were produced in low yield along with the C-13 hydroxy derivatives of adriamycin and daunomycin as by-products. The 3'-morpholino derivatives are reported to have significantly greater antitumor potency (vs P-388 leukemia in mice) than the adriamycin and daunomycin starting materials.

The present inventors have discovered a new and more efficient process for preparing the 3'-deamino-3'-morpholino-adriamycin and -daunomycin derivatives in high yields without contamination with the C-13 hydroxy by-products produced in the prior art process. In addition, they have discovered that their new N-alkylation procedure can be used to produce 3'-deamino-3'-morpholino-carminomycin and that this new carminomycin derivative possesses potent antitumor activity and also antimicrobial activity.

The 3'-deamino-3'-morpholino-adriamycin, -daunomycin and -carminomycin derivatives may be produced by reacting adriamycin, daunomycin or carminomycin, respectively (or acid addition salts thereof), with bis(2-haloethyl)ether of the formula III, preferably in the presence of base.

The starting material anthracycline glycosides may be in free base form or in the form of an acid addition salt. Since acid addition salts of the end-products may be converted by known methods to the corresponding free base products or to pharmaceutically acceptable acid addition salts, it is not necessary for the starting material salt to be nontoxic (pharmaceutically acceptable).

The reagents bis(2-iodoethyl)ether and bis(2-bromoethyl)ether used in the above process may be readily obtained in quantitative yield from commercially available bis(2-chloroethyl)ether and NaI or NaBr (J. Chem. Soc., pg. 2525–2530, 1930).

The N-alkylation of the appropriate anthracycline glycoside starting material or acid addition salt thereof is carried out in an inert polar solvent such as N,N-dimethylformamide (DMF), dimethylsulfoxide, hexamethylphospholamide, glyme, tetrahydrofuran, dioxane, and the like. The most preferred solvent is DMF. The solvents can be used in the presence of a small amount of water, but anhydrous solvents are most desirable. The reaction is preferably carried out in the presence of a base such as triethylamine. The amount of base used in the reaction is not critical, but in general, we prefer to use at least two moles, preferably 2.5 to 4 moles, of base per mole of starting material II. The bis(2-haloethyl)ether of formula III is preferably used in a molar excess relative to starting material II, i.e. at least 1.5 moles, preferably 15 to 30 moles, per mole of compound II. The temperature is not critical, and the reaction can be carried out advantageously at 0° to 80° C., most preferably at about room temperature. The reaction may be terminated after about 10 to 50 hours under the above-identified preferred reaction conditions.

The end-products of formula I may be isolated and purified by methods known per se for other anthracycline glycosides. The products obtained in the form of the free base compound may be converted to a pharmaceutically acceptable acid addition salt by treating it with a nontoxic inorganic acid such as HCl, $H_2SO_4$, $H_3PO_4$, etc. or a nontoxic organic acid such as acetic acid, propionic acid, maleic acid, oleic acid, palmitic acid, citric acid, succinic acid, tartaric acid, fumaric acid, glutamic acid, pantothenic acid and laurylsulfonic acid. Products in the form of an acid addition salt may be converted to the corresponding free base by neutralization with a basic substance. Finally, toxic acid addition salts may be converted to nontoxic acid addition salts by neutralization and treatment with a nontoxic acid as described above. The pharmaceutically acceptable salts and free base form of 3'-deamino-3'-morpholino-carminomycin are substantially equivalent in antimicrobial and antitumor properties.

Biological Properties

The novel 3'-deamino-3'-morpholino-carminomycin of the present invention (including pharmaceutically acceptable acid addition salts thereof) has been found to possess antimicrobial activity against a variety of pathogenic microorganisms. To illustrate such activity, minimum inhibitory concentrations (as determined by the broth dilution method) of the compound against several bacteria are shown in the Table below.

TABLE I

| Minimum Inhibitory Concentration (MIC, mcg/ml) | |
| --- | --- |
| Bacteria | 3'-Deamino-3'-morpholino-carminomycin |
| Staph. aureus FDA 209P | 0.78 |
| Staph. aureus Smith | 6.25 |
| Bacillus subtilis NRRL B-558 | 1.56 |
| Bacillus cereus ATCC 10702 | 0.78 |
| Sarcina lutea PCI 1001 | 0.78 |
| Micrococcus flavus FDA 16 | 1.56 |
| Corynebacterium bovis 1810 | 0.39 |
| Pseudomonas aeruginosa A3 | >100 |

As indicated by Table I, 3'-deamino-3'-morpholino-carminomycin is useful as an antimicrobial agent, particularly against Gram-positive bacteria.

The antitumor activity of 3'-deamino-3'-morpholino-carminomycin thereof can be demonstrated by the following experiments.

(A) Activity of inhibiting growth, DNA synthesis and RNA synthesis of cultivated leukemic cells L1210 of mice.

3'-Deamino-3'-morpholino-carminomycin markedly inhibit the growth and nucleic acid synthesis of cultivated leukemic cells L1210 of mice. For example, L1210 cells were inoculated in a concentration of $5 \times 10^4$/ml in an RPMI 1640 culture medium containing

Preparation of Starting Material

Process for Producing Bis(2-iodoethyl)ether

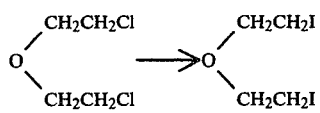

Bis(2-chloroethyl)ether (1.43 g; about 10 mmoles) and NaI (6 g; about 40 mmoles) were dissolved in 20 ml of acetone and refluxed by heating at 60°–70° C. for 24 hours. After the reaction, acetone was evaporated and the reaction mixture was dissolved in 30 ml of n-hexane, washed with 20 ml of water three times and dried over sodium sulfate. After concentration of the n-hexane layer, 3.1 g (almost theoretical yield) of an oily and colorless compound was obtained. The compound, bis(2-iodoethyl)ether could be used in the following examples without further purification.

EXAMPLE 1

Process for Producing 3′-Deamino-3′-morpholinodaunomycin

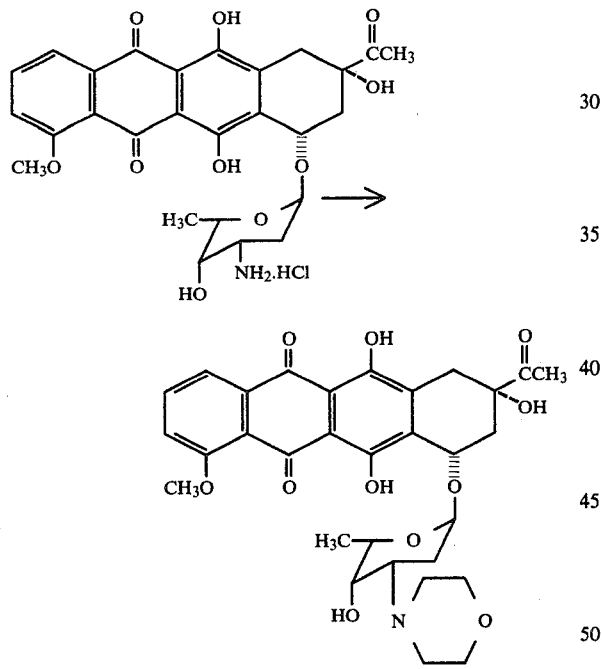

To a solution of daunomycin hydrochloride (20 mg; 0.035 mmoles) in 1 ml of DMF were added 200 mg (0.614 mmoles) of bis(2-iodoethyl)ether and 0.015 ml (0.107 mmoles) of triethylamine, and the reaction was carried out for 36 hours at room temperature. After the reaction, the reaction mixture was added to 20 ml of water and extracted three times with 20 ml of chloroform. The chloroform layer was washed with 20 ml of water three times, dried over anhydrous sodium sulfate and concentrated to dryness.

The crude compound was purified by preparative thin-layer chromatography (TLC) (chloroform-methanol, 9:1 v/v) and 14 mg (yield: about 64% of the title compound was obtained.

Physico-chemical properties of the compound thus obtained:

(1) Silica gel thin-layer chromatography, chloroform-methanol mixture (9:1 v/v): Rf=0.58

(2) Melting point: 139°–145° C.

(3) $[\alpha]_D^{22} = +325°$ (c 0.1, acetone)

(4) NMR (90 MHz, CDCl$_3$)

| $\gamma$ (ppm) | |
|---|---|
| 14.03 | (1H, s, phenolic OH) |
| 13.30 | (1H, s, phenolic OH) |
| 8.06 | (1H, d.d, H-1) |
| 7.80 | (1H, t, H-2) |
| 7.40 | (1H, d.d, H-3) |
| 5.56 | (1H, m, H-1′) |
| 5.30 | (1H, m, H-7) |
| 4.66 | (1H, s, 9-OH) |
| 4.10 | (3H, s, 4-OCH$_3$) |
| 4.07 | (1H, dq, H-5′) |
| ca 3.7 | (1H, H-4′) (4H, O(CH$_2$—CH$_2$)$_2$N—) |
| 3.10 | (2H, AB, H-10) |
| 2.40 | (3H, s, $-\overset{O}{\underset{\|}{C}}-CH_3$) |
| 1.38 | (3H, d, H-6′) |
| 2.7–1.6 | (1H, H-3′) (4H, O(CH$_2$—CH$_2$)$_2$N—) (2H, H-8) (2H, H-2′) |

EXAMPLE 2

Process for Producing 3′-Deamino-3′-morpholino-adriamycin

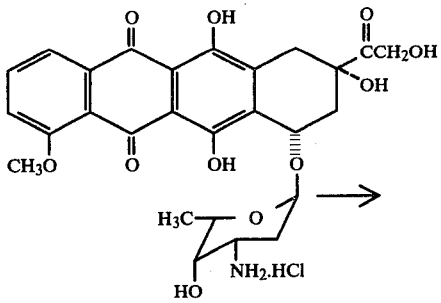

20% calf serum (Rosewell Memorial Park Institute 1640), and simultaneously 3'-deamino-3'-morpholino-carminomycin was added in various concentrations. Thus, the cells were cultivated in an incubator containing carbon dioxide gas at 37° C. The 50% growth inhibitory concentration with respect to a control group was determined.

Separately, the above cultivated cells L1210 were suspended in a concentration of $1 \times 10^5$/ml in an RPMI 1640 medium containing 10% of calf serum, and cultivated for 1 to 2 hours in an incubator containing carbon dioxide gas at 37° C. Then, 3'-deamino-3'-morpholino-carminomycin was added in various concentrations, and 15 minutes later, $^{14}C$-uridine (0.05 μCi/ml) and $^{14}C$-thymidine (0.05 μCi/ml) were added. Thus, the cells were cultivated at 37° C. for 60 minutes. A 10% aqueous solution of trichloroacetic acid was added to the reaction liquor to stop the reaction and simultaneously precipitate an acid-insoluble matter. The acid-insoluble matter was washed three times with a 10-5% aqueous solution of trichloroacetic acid, and then dissolved in formic acid. The radioactivity of the acid-insoluble matter was measured. From the ratio of incorporated radiation to that of a control group, the concentrations which inhibited radiation by 50% were measured. The results are shown in Table II.

TABLE II

Activity of 3'-deamino-3'-morpholino-carminomycin to inhibit the growth, DNA synthesis and RNA synthesis of cultivated leukemic cells L1210 of mice

| Compound | IC$_{50}$ (μg/ml) | | | |
|---|---|---|---|---|
| | 1 day after | 2 days after | DNA | RNA |
| 3'-Deamino-3'-morpholino-carminomycin | 0.010 | 0.0009 | 0.09 | 0.013 |

(B) Antitumor activity on CDF$_1$ mouse leukemia induced by leukemic cells L1210 of mice.

Leukemic cells L1210 of mice were intraperitoneally transplanted in an amount of $1 \times 10^5$ per mouse in CDF$_1$ mice. Starting 24 hours after the transplantation, 3'-deamino-3'-morpholino-carminomycin was intraperitoneally or orally administered to the mice for 10 consecutive days. The survival rate (T/C, %) was calculated in comparison with a control group (to which physiological saline was administered). The results are shown in Table III.

TABLE III

Antitumor activity (T/C % of the survival period) on L1210

| Compound | Route of administration | Dosage (μg/mouse/day) | | | | | |
|---|---|---|---|---|---|---|---|
| | | 12.5 | 6.25 | 3.125 | 1.56 | 0.78 | 0.39 |
| 3'-Deamino-3'-morpholino-carminomycin | i.p. | 194* | 122 | 122 | 94 | 122 | 94 |
| | p.o. | — | — | 206 | 167 | 133 | 106 | 111 | 100 |

*Toxic (C) Acute toxicity by oral administration on CDF$_1$ mouse. The acute toxicity by oral administration when examined in CDF$_1$ mouse: LD$_{50}$ 1.56 mg/kg.

Therapeutic Use

As indicated above, the 3'-deamino-3'-morpholino-carminomycin and pharmaceutically acceptable acid addition salts thereof are novel antibiotics, useful in both human and veterinary medicine, and also possess marked inhibitory acticity against malignant tumors in experimental animals, including both solid and ascitic types.

According to one aspect of the invention, a method is provided for therapeutically treating a mammalian host affected by a microbial infection (particularly a Gram-positive bacterial infection) or by a malignant tumor (i.e. a solid or ascitic type tumor such as L1210 leukemia) which comprises administering to said host an effective antimicrobial or tumor-inhibiting dose of 3'-deamino-3'-morpholino-carminomycin or a pharmaceutically acceptable acid addition salt thereof.

According to another aspect of the invention, a pharmaceutical composition is provided which comprises a therapeutically effective antimicrobial or tumor-inhibiting amount of 3'-deamino-3'-morpholino-carminomycin or a pharmaceutically acceptable acid addition salt thereof in combination with a pharmaceutical carrier or diluent. Such compositions may be made up in any pharmaceutical form appropriate for oral or parenteral administration.

For oral administration, either solid or fluid dosage forms can be prepared such as, for example, tablets, capsules, pills, powders, granules, oral syrups, oral solutions or oral suspensions. For parenteral administration, fluid dosage forms are prepared utilizing the active compound and a sterile vehicle. The compound, depending on the vehicle and concentration used, can be either suspended or dissolved in the vehicle. The parenteral dosage forms may be manufactured in the form of sterile solid compositions for reconstitution with sterile water, physiological saline or some other sterile injectable medium prior to administration.

An effective quantity of the active compound is employed in treatment. For use as an antimicrobial agent, the compound or pharmaceutical composition thereof is in general administered so that the concentration of active ingredient is greater than the minimum inhibitory concentration for the particular organism being treated. For use as an antitumor agent, the dosage to be used for a given host can be ascertained using known dosage ranges for adriamycin, daunomycin and carminomycin modified by the relative activities of 3'-deamino-3'-morpholino-carminomycin and these known anthracyclines as shown by experimental animal tumor testing. It will be appreciated that the actual preferred dosage amounts used will vary according to the particular compound being used, the particular composition formulated, the mode of application and the particular situs, host and disease being treated. Many factors that modify the action of the drug will be taken into account by those skilled in the art, for example, age, body weight, sex, diet, route of administration, time of administration, rate of excretion, condition of the host, drug combinations, reaction sensitivities and severity of the disease. Administration can be carried out continuously or periodically within the maximum tolerated dose.

The following examples are provided for illustrative purposes only and are not intended to limit the scope of the invention.

-continued

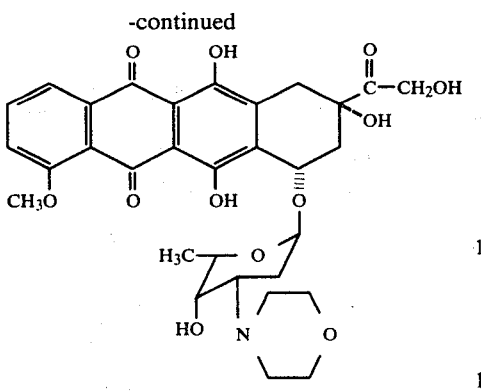

To a solution of adriamycin hydrochloride (20 mg; 0.034 mmoles) in 1 ml of DMF were added 200 mg (0.614 mmoles) of bis(2-iodoethyl)ether and 0.014 ml (0.104 mmoles) of triethylamine, and the reaction was carried out for 36 hours at room temperature. The product was worked up in the same way as in the purification procedure of Example 1 to give 13 mg (yield 61%) of the title compound.

Physico-chemical properties of the compound thus obtained:

(1) Silica gel thin-layer chromatography, chloroform-methanol mixture (9:1 v/v): Rf=0.47

(2) Melting point: 154°–160° C.

(3) $[\alpha]_D^{22} = +300°$ (c 0.1, acetone)

(4) NMR (the same as Example 1)

| γ (ppm) | |
|---|---|
| 13.97 | (1H, s, phenolic OH) |
| 13.21 | (1H, s, phenolic OH) |
| 8.04 | (1H, d.d, H-1) |
| 7.79 | (1H, t, H-2) |
| 7.40 | (1H, d.d, H-3) |
| 5.55 | (1H, m, H-1') |
| 5.30 | (1H, m, H-7) |
| 4.76 | (2H, s, H-14) |
| 4.72 | (1H, s, 9-OH) |
| 4.07 | (3H, s, 4-OCH₃) |
| 3.97 | (1H, d.q, H-5') |
| ca 3.7 | { (1H, H-4') <br> (4H, O⟨CH₂CH₂⟩N—) <br> ⟨CH₂CH₂⟩ } |
| 3.10 | (2H, AB, H-10) |
| 1.37 | (3H, d, H-6') |
| 2.9–1.6 | { (1H, H-3') <br> (4H, O⟨CH₂CH₂⟩N—) <br> ⟨CH₂CH₂⟩ <br> (2H, H-8) <br> (2H, H-2') } |

EXAMPLE 3

Process for Producing 3'-Deamino-3'-morpholino-carminomycin

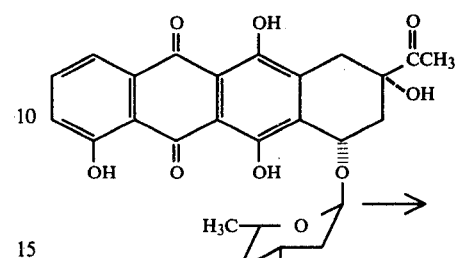

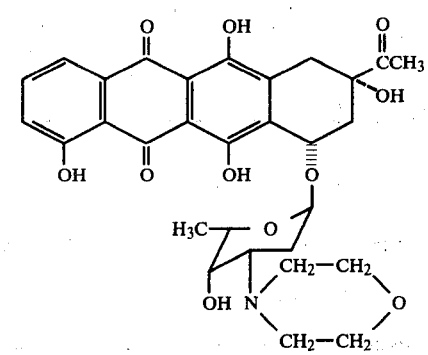

To a solution of carminomycin hydrochloride (20 mg; 0.036 mmoles) in 1 ml of DMF were added 200 mg (0.614 mmoles) of bis(2-iodoethyl)ether and 0.014 ml (0.104 mmoles) of triethylamine, and the reaction was carried out for 36 hours at room temperature. The product was worked up in the same way as in the purification procedure of Example 1 to give 10 mg (yield 47%) of the title compound.

Physico-chemical properties of the compound thus obtained:

(1) Silica gel thin-layer chromatography, chloroform-methanol mixture (5:1 v/v: Rf=0.91

(2) Melting point: 130°–137° C.

(3) $[\alpha]_D^{22} = +200°$ (c 0.1, acetone)

(4) NMR (as in Example 1)

| δ (ppm) | |
|---|---|
| 13.42 | (1H, s, phenolic OH) |
| 12.90 | (1H, s, phenolic OH) |
| 12.08 | (1H, s, phenolic OH) |
| 7.85 | (1H, d.d, H-1) |
| 7.70 | (1H, t, H-2) |
| 7.28 | (1H, d.d, H-3) |
| 5.53 | (1H, m, H-1') |
| 5.25 | (1H, m, H-7) |
| 4.65 | (1H, s, 9-OH) |
| 4.07 | (1H, d.q, H-5') |
| ca 3.7 | { (1H, H-4') <br> (4H, O⟨CH₂CH₂⟩N—) <br> ⟨CH₂CH₂⟩ } |
| 3.12 | (2H, AB, H-10) |

-continued

| δ (ppm) | |
|---|---|
| 2.40 | (3H, s, —C(=O)CH₃) |
| 1.38 | (3H, d, H-6') |
| 2.8–1.6 | (1H, H-3'); (4H, O(CH₂CH₂)₂N—); (2H, H-8); (2H, H-2') |

The Rf values of the anthracycline derivatives prepared in Examples 1-3 on TLC with chloroform-methanol (5:1 v/v) are shown below with the corresponding values for daunomycin, adriamycin and aclacinomycin.

| Compound | Rf values |
|---|---|
| Daunomycin | 0.07 |
| Adriamycin | 0.02 |
| Aclacinomycin | 0.88 |
| 3'-Deamino-3'-morpholino-daunomycin | 0.89 |
| 3'-Deamino-3'-morpholino-adriamycin | 0.78 |
| 3'-Deamino-3'-morpholino-carminomycin | 0.91 |

Comparison of the Rf values of the compounds of formula I with that of orally active aclacinomycin suggests that the formula I compounds, including 3'-deamino-3'-morpholino-carminomycin, may be used orally as well as parenterally.

We claim:

1. The anthracycline glycoside 3'-deamino-3'-morpholino-carminomycin of the formula

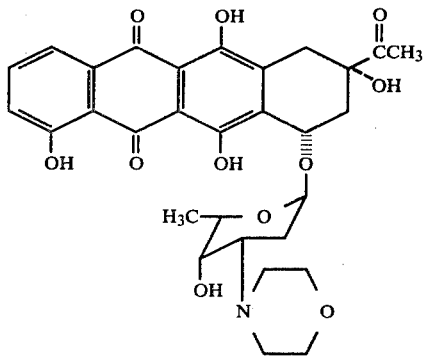

or a pharmaceutically acceptable acid addition salt thereof.

2. A process for preparing an anthracycline glycoside of the formula

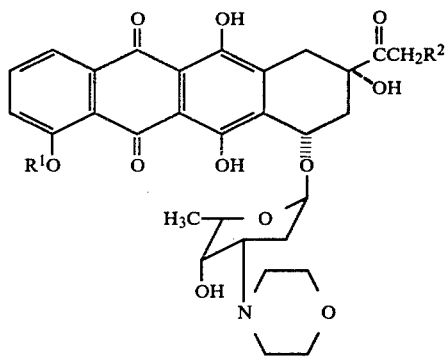

wherein $R^1$ represents H of CH₃ and $R^2$ represents H or OH, provided that when $R^1$ is H, $R^2$ is H, or an acid addition salt thereof, which process comprises reacting a compound of the formula

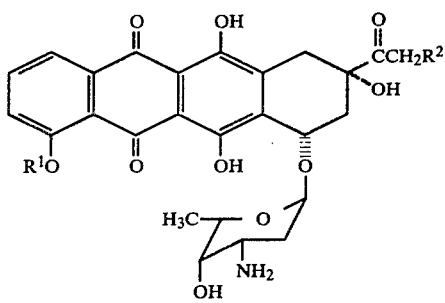

wherein $R^1$ and $R^2$ are as defined above, or an acid addition salt thereof, with a compound of the formula

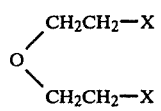

wherein X represents Br or I.

* * * * *